United States Patent

Miyamoto et al.

[11] Patent Number: 5,958,199
[45] Date of Patent: *Sep. 28, 1999

[54] BIOSENSOR

[75] Inventors: Yoshiko Miyamoto; Toshihiko Yoshioka; Shiro Nankai, all of Hirakata, Japan

[73] Assignee: Matsushita Electric Industrial Co., Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/815,760

[22] Filed: Mar. 12, 1997

[30] Foreign Application Priority Data

Mar. 13, 1996 [JP] Japan ................................. 8-055925

[51] Int. Cl.$^6$ .................................................. G01N 27/26
[52] U.S. Cl. ........................................... 204/403; 435/817
[58] Field of Search .................................. 204/403, 416; 435/817; 205/777.5

[56] References Cited

U.S. PATENT DOCUMENTS

| | | | |
|---|---|---|---|
| 5,288,613 | 2/1994 | Luong et al. | 435/25 |
| 5,320,725 | 6/1994 | Gregg et al. | 205/777.5 |
| 5,575,895 | 11/1996 | Ikeda et al. | 204/403 |
| 5,672,256 | 9/1997 | Yee | 204/403 |
| 5,708,247 | 1/1998 | McAleer et al. | 204/403 |

FOREIGN PATENT DOCUMENTS

| | | |
|---|---|---|
| 0 429 076 A2 | 5/1991 | European Pat. Off. . |
| 3-202764 | 9/1991 | Japan . |
| 07209243 | 11/1995 | Japan . |

OTHER PUBLICATIONS

European Search Report for Application No. 97301402.0–2116–dated Oct. 22, 1998.
Kawaguri Et al. ("Disposable Glucose Sensor Employing Potassium Ferricyanide as a Mediator", Denki Kagaku Ouobi Kogyo Butsuri Kagaku,58(12), 1990, 1119–1124).

*Primary Examiner*—Robert Warden
*Assistant Examiner*—Alex Naguerola
*Attorney, Agent, or Firm*—McDermott, Will & Emery

[57] ABSTRACT

Disclosed is a high performance biosensor free from the effect of any components existing in a sample solution other than a substrate. The biosensor comprises an electrically insulating base plate, an electrode system including a working electrode and a counter electrode provided on the base plate, and a reaction layer containing a hydrophilic polymer, an enzyme and an electron acceptor located over the electrode system. The reaction layer contains an excess amount of hydrophilic polymer in a range of 150 to 1,000% by weight of the enzyme.

6 Claims, 2 Drawing Sheets

BIOSENSOR

BACKGROUND OF THE INVENTION

The present invention relates to a biosensor for facilitating rapid quantitation of a specific component contained in a biological sample with high accuracy.

So far, various biosensors have been developed as a system for facilitating simple quantitation of a specific component contained in a sample, without necessitating dilution or agitation of a sample solution.

Biosensors utilizing enzyme reaction use a carrier that carries or contains an enzyme reaction system. These biosensors use light, color, or electrical signal as a means for signal transmission.

An example of the biosensor utilizing the electrical signal as a signal transmitter is disclosed in Japanese Laid-Open Patent Publication Hei 3-202764, wherein an electrode system comprised of a working electrode and a counter electrode is formed on an electrically insulating base plate by screen printing or the like, followed by formation of an electrically insulating layer thereon, then an enzyme reaction layer containing a hydrophilic polymer, an oxidoreductase, and an electron acceptor is formed over the above-mentioned electrode system. Addition of drops of a sample solution containing a substrate as a measuring substance on the enzyme reaction layer causes dissolution of the enzyme reaction layer. As a result, reaction between the substrate and the enzyme proceeds, and the substrate is oxidized, which in turn promotes reduction of the electron acceptor. At completion of the enzyme reaction, the reduced electron acceptor is electrochemically oxidized, and a current level for oxidation measured at that time is used to determine the concentration of the substrate contained in the sample solution.

The biosensor having the above-described conventional structure, however, has a drawback that a response of the biosensor may vary by the presence of any components contained in the sample solution other than the substrate, even when the sample solution contains the substrate at an equal concentration. Taking an example, the presence of a substance in the sample solution which affects pH value often causes a change in enzyme activity, thereby varying the response of the biosensor. In the case of blood sample that contains particle components such as red blood cells, for example, a difference in the concentration of such particle components causes a difference in the sensor response.

An effective method to relieve the difference in the nature of the sample solution is to decrease this difference by diluting the sample solution using a dilute solution. However, this method is not necessarily advantageous from the aspect of ease of operation.

BRIEF SUMMARY OF THE INVENTION

The present invention provides a biosensor comprising an electrically insulating base plate, an electrode system including a working electrode and a counter electrode provided on the electrically insulating base plate, and a reaction layer containing a hydrophilic polymer, an enzyme, and an electron acceptor located over the electrode system, wherein a concentration of the hydrophilic polymer in the reaction layer is in a range of 150 to 1,000% by weight of the enzyme.

In a preferred mode of the present invention, the hydrophilic polymer is selected from the group consisting of cellulose ethers, such as carboxymethyl cellulose, carboxyethyl cellulose, hydroxyethyl cellulose, hydroxypropyl cellulose, carboxyethylmethyl cellulose, and the like, amylose, and starch.

In another preferred mode of the present invention, the enzyme is selected from the group consisting of glucose oxidase, glucose dehydrogenase, alcohol oxidase, alcohol dehydrogenase, cholesterol oxidase, cholesterol dehydrogenase, lactate oxidase, lactate dehydrogenase, fructose dehydrogenase, ascorbate oxidase, and bilirubin oxidase.

In still another preferred mode of the present invention, the reaction layer is composed of a first layer containing the hydrophilic polymer and a second layer containing the hydrophilic polymer, the enzyme and the electron acceptor.

In still another preferred mode of the invention, the hydrophilic polymer included in the first layer is selected from the group consisting of carboxymethyl cellulose, carboxyethyl cellulose, hydroxyethyl cellulose, hydroxypropyl cellulose, and carboxyethylmethyl cellulose.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

In the following, the present invention will be described more specifically with reference to examples.

Figure 1:
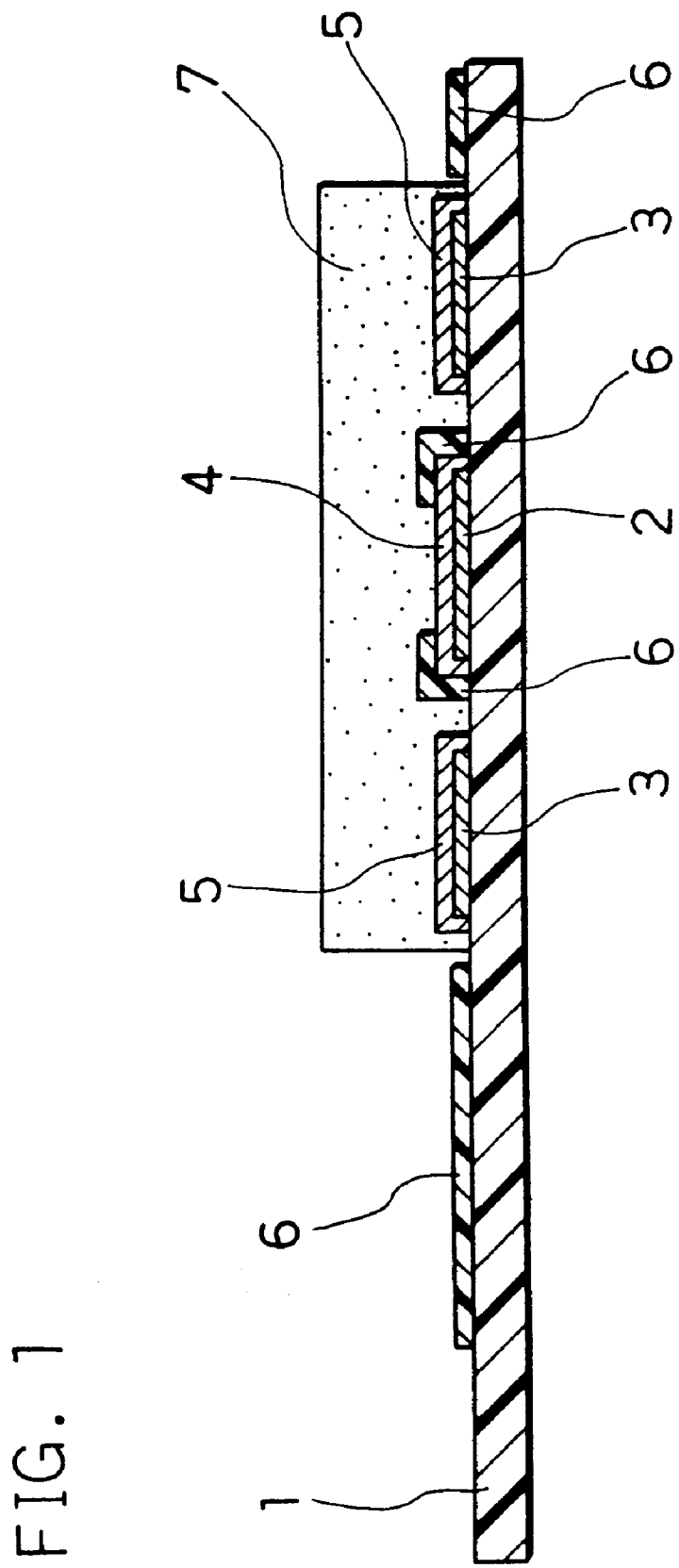
FIG. 1 is a schematic cross-sectional view of a glucose sensor in accordance with the present invention, omitting a cover and a spacer therefrom.

FIG. 1 is a schematic cross-sectional view illustrating a biosensor in accordance with the present invention, omitting the cover and spacer therefrom.

First, leads 2 and 3 are formed by printing a silver paste using the screen printing method on an electrically insulating base plate 1 made of polyethylene terephthalate. Then, an electrode system comprising a working electrode 4 and a counter electrode 5 made of a resin binder-containing electrically conductive carbon paste and an electrically insulating layer 6 made of an electrically insulating paste are formed using the same printing method.

The electrically insulating layer 6 functions to hold areas of exposed portions of the working electrode 4 and the counter electrode 5 constant, and covers part of the leads 2 and 3.

After formation of the above-mentioned electrode-related segment, an aqueous solution of a hydrophilic polymer carboxymethyl cellulose (hereafter abbreviated to "CMC") is dropped over the surface of the electrode system and the resultant is dried to form a first layer. Then, an aqueous solution of a mixture of the enzyme, electron acceptor and hydrophilic polymer is dropped over the first layer and dried to form a second layer containing the enzyme, electron acceptor and hydrophilic polymer. In this way, a reaction layer 7 composed of the first layer and the second layer is formed.

As stated previously, addition of drops of an aqueous solution of a mixture of the enzyme, electron acceptor and hydrophilic polymer over the first layer causes temporary dissolution of the originally formed first layer. The hydrophilic polymer in the dissolved first layer is mixed in part with the enzyme and other substances in the second layer and the mixture was dried in a half-mixed state to form the reaction layer 7 containing the enzyme, electron acceptor and hydrophilic polymer. However, since agitation is not applied after addition of drops of the aqueous solution, the mixing does not proceed completely. This renders the surface of the electrode system covered only with the hydrophilic polymer CMC. The presence of the first layer containing the hydrophilic polymer effectively prevents adsorbance of protein onto the surface of the electrode system.

Figure 2:
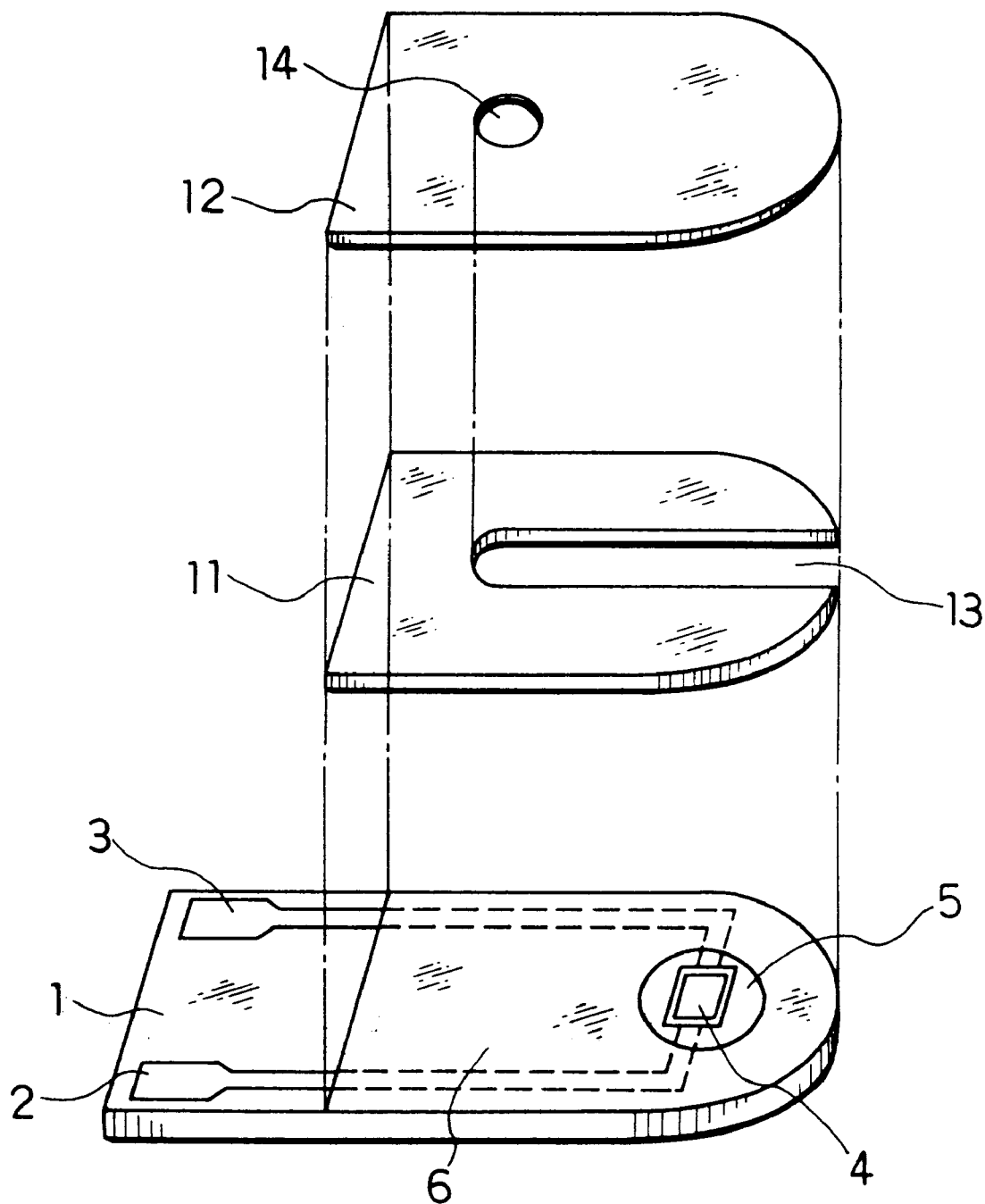
FIG. 2 is an exploded perspective view of the same glucose sensor, omitting a reaction layer therefrom.

After formation of the reaction layer in this way, a cover 12 and a spacer 11 are adhered to the electrically insulating base plate 1 in a positional relationship as shown by a dotted line in FIG. 2. This gives a glucose sensor.

The biosensor having the above-mentioned construction alleviates an adverse effect caused by the nature of the sample solution, such as induction of a difference in pH, with the aid of the action of the hydrophilic polymer, which results in a decrease in variations of the sensor response induced by any components existing in the sample solution other than the substrate, or by the difference in their concentration.

The biosensor in accordance with the present invention responds to both types of sample, blood and aqueous solution of glucose, and provides a substantially equivalent current value with both samples. This is because the biosensor alleviates the effect on the sensor response by the presence of red blood cells and serum protein in blood, and prevents migration of large particle components such as hemocytes into the reaction layer, thereby trapping them at the level of the surface of the reaction layer.

The above-mentioned effects can be obtained when the hydrophilic polymer is contained in the reaction layer in a range of 150 to 1,000% by weight of the enzyme. A concentration of the hydrophilic polymer of less than 150% by weight of the enzyme results in unsatisfactory alleviation of the influence by the presence of the components other than the substrate on the sensor response. Otherwise, a concentration of the hydrophilic polymer exceeding 1,000% by weight of the enzyme makes it very difficult to cause dissolution of the reaction layer in the sample solution, which prolongs the time required for satisfactory measurement of the sensor response, and increases variations in the measured values of the sensor response.

Although the concentration of the enzyme in the reaction layer is varied depending on the type of enzyme, an appropriate content may be 3 to 300 units per 1 $cm^2$ of the working electrode. In a disposable sensor having a construction as shown in the below-mentioned example, the content of the enzyme in the reaction layer ranges from 0.1 to 10 units, that is, 0.5 to 50 $\mu g$ in weight in the case of representative glucose oxidase.

In the following, specific examples of the present invention will be described.

EXAMPLE 1

Here, a glucose sensor is taken as an example of the biosensor.

As shown in FIG. 1, the leads 2 and 3, the electrode system comprising the working electrode 4 and the counter electrode 5, and the electrically insulating layer 6 were formed on the electrically insulating base plate 1 made of polyethylene terephthalate.

After the electrode-related segment was formed, 5 $\mu l$ of a 0.25 wt % aqueous solution of a hydrophilic polymer carboxymethyl cellulose (CMC) was dropped over the surface of the electrode system, followed by drying for 10 min in a hot dryer at 50° C. to form the first layer. A second layer was formed over the first layer thus formed by dropping 4 $\mu l$ of an aqueous solution of a mixture prepared by dissolving 10 mg of an enzyme glucose oxidase (EC1.1.3.4; hereafter abbreviated to "GOD"), 16 mg of an electron acceptor potassium ferricyanide, and 20 mg of the hydrophilic polymer CMC in 1 ml of water and the resultant was dried for 10 min in a hot dryer at 50° C. to form the reaction layer 7 containing the hydrophilic polymer, enzyme and electron acceptor. Total CMC contained in the first layer and the second layer of the reaction layer amounts to 231% by weight of the glucose oxidase. The amount of glucose oxidase is about 40 $\mu g$ (equivalent to about 8 units).

After forming the reaction layer in the above-mentioned manner, the cover 12 and the spacer 11 were adhered to the electrically insulating base plate 1 in a positional relationship as shown by the dotted line in FIG. 2. This gave a glucose sensor of Example 1.

Sample solutions for the glucose sensor were glucose solutions containing glucose at a concentration of 0 to 800 mg/dl, which were formulated with pure water, 100 mM phosphate buffer solution at pH5, or 100 mM phosphate buffer solution at pH7. When the sample solution (3 $\mu l$) is supplied from an opening of a slit 13 on the spacer which serves as a sample supply port, the sample solution passes through a sample supply path defined by the slit 13 up to the level of an air vent 14. Then, the sample solution infiltrates the reaction layer 7, which causes dissolution of the reaction layer 7. The glucose contained in the sample solution is oxidized by the glucose oxidase at the reaction layer 7. As a result, transferred electrons cause a reduction of the potassium ferricyanide, which produces potassium ferrocyanide, and the potassium ferrocyanide thus formed are transferred proximal to the surface of the electrode system.

One min after the sample was supplied, a voltage of +0.5 V was applied between the working electrode 4 and the counter electrode 5 of the electrode system. Measurement of a current value after 5 sec showed that the obtained values were dependent on the glucose concentration in the glucose solution formulated with pure water, 100 mM phosphate buffer solution at pH5, or 100 mM phosphate buffer solution at pH7. Current values responsive to the glucose concentrations in the glucose solutions formulated with pure water (hereafter referred to as "pure water glucose solution"), 100 mM phosphate buffer solution at pH5 (hereafter referred to as "PBS glucose solution pH5"), or 100 mM phosphate buffer solution at pH7 (hereafter referred to as "PBS glucose solution pH7") were almost equal.

Blood was used as another sample solution for the glucose sensor. One min after sample supply, a voltage of +0.5 V was applied between the working electrode 4 and the counter electrode 5 of the electrode system. Similarly, measurement of the current value after 5 sec showed current values dependent on the glucose concentration in the blood sample solution. The current value responsive to the glucose concentration in the blood sample solution was about 98% of the current value responsive to the glucose solution of the same glucose concentration.

COMPARATIVE EXAMPLE 1

For comparison, a glucose sensor having the same construction as in Example 1 was prepared, except that the enzyme and the electron acceptor were added to the mixture for forming the second layer of the reaction layer, omitting the hydrophilic polymer. The content of CMC in the first layer of the reaction layer was 31% by weight of the glucose oxidase. With the glucose sensor of Comparative Example 1, the current value responsive to the glucose concentration in the PBS glucose solution pH5 was substantially the same as that of the pure water glucose solution. However, the current value responsive to the glucose concentration in the PBS glucose solution pH7 was about 60 to 70% of that of the pure water glucose solution, indicating no linear relationship between the current value and the glucose concentration. The current value responsive to the glucose concentration in the blood sample solution was about 70 to 80% of that of the pure water glucose solution of the same glucose concentration. The results suggested that a low responsive current value increases S/N ratio, which causes a decrease in the measurement accuracy of the sensor, and that individual difference in blood hematocrit level causes an adverse effect on the current value of the sensor in response to the glucose concentration.

EXAMPLE 2

Following the same procedure as in Example 1, the leads 2 and 3, the electrode system comprising the working electrode 4 and counter electrode 5, and the electrically insulating layer 6 were formed on the electrically insulating base plate 1 made of polyethylene terephthalate.

In a manner similar to Example 1, after forming the first layer containing the hydrophilic polymer, the second layer was formed thereon, using an aqueous solution of a mixture prepared by dissolving 50 mg of hydroxyethyl cellulose, 10 mg of GOD, and 16 mg of potassium ferricyanide in 1 ml water to form the reaction layer 7 containing the hydrophilic polymer, enzyme and electron acceptor. The total content of the hydrophilic polymer in the first and the second layer amounted to 531% by weight of the glucose oxidase.

Then, the cover 12 and spacer 11 were adhered to the electrically insulating base plate 1 as in Example 1. This gave a glucose sensor of Example 2.

Sample solutions for the glucose sensor were glucose solutions containing glucose at a concentration of 0 to 800 mg/dl, formulated with pure water, 100 mM phosphate buffer solution at pH5, or 100 mM phosphate buffer solution at pH7. As in Example 1, one min after supply of the sample solution (3 $\mu$l) from the sample supply port, a voltage of +0.5 V was applied between the working electrode 4 and the counter electrode 5 of the electrode system. Measurement of a current value after 5 sec showed that the obtained values were dependent on the glucose concentrations in the glucose solutions formulated with pure water, 100 mM phosphate buffer solution at pH5, or 100 mM phosphate buffer solution at pH7. The current value responsive to the glucose concentration was substantially equal between the pure water glucose solution, PBS glucose solution pH5 and PBS glucose solution pH7.

Blood was used as another sample solution for the glucose sensor. One min after sample supply, a voltage of +0.5 V was applied between the working electrode 4 and the counter electrode 5 of the electrode system. Similarly, measurement of the current value after 5 sec showed a current value dependent on the glucose concentration in the blood sample solution. The current value responsive to the glucose concentration in the blood sample solution was about 96% of the current value responsive to the glucose solution of the same glucose concentration.

COMPARATIVE EXAMPLE 2

In the same manner as in Example 1, after forming the first layer containing the hydrophilic polymer, the second layer was formed thereon, using an aqueous solution of a mixture prepared by dissolving 12 mg of hydroxyethyl cellulose, 10 mg of GOD, and 16 mg of potassium ferricyanide in 1 ml water to form the reaction layer 7 containing the hydrophilic polymer, enzyme and electron acceptor. The total content of the hydrophilic polymer in the first and the second layer amounted to 131% by weight of the glucose oxidase.

Then, the cover 12 and spacer 11 were adhered to the electrically insulating base plate 1 as in Example 1. This gave a glucose sensor of Comparative Example 2.

In a manner similar to Example 1, one min after supply of the sample solution (3 $\mu$l) from the sample supply port 13, a voltage of +0.5 V was applied between the working electrode 4 and the counter electrode 5 of the electrode system. Measurement of a current value after 5 sec showed that the obtained values were dependent on the glucose concentrations in the glucose solutions formulated with pure water, 100 mM phosphate buffer solution at pH5, or 100 mM phosphate buffer solution at pH7. The current value responsive to the glucose concentration in the PBS glucose solution pH5 was substantially the same as that of the pure water glucose solution. Whereas, the current value responsive to the glucose concentration in the PBS glucose solution pH7 was about 60 to 70% of that of the pure water glucose solution, indicating no linear relationship between the current value and the glucose concentration. The current value responsive to the glucose concentration in the blood sample solution was about 75 to 85% of that of the pure water glucose solution of the same glucose concentration. The results suggested that a low current value increases S/N ratio, which causes a decrease in the measurement accuracy of the sensor, and that individual difference in blood hematocrit level causes an adverse effect on the current value of the sensor.

EXAMPLE 3

Following the same procedure as in Example 1, after forming the first layer containing the hydrophilic polymer, the second layer was formed thereon, using an aqueous solution of a mixture prepared by dissolving 10 mg of GOD, 16 mg of potassium ferricyanide and 20 mg of carboxyethyl cellulose in 1 ml water to form the reaction layer 7 containing the hydrophilic polymer, enzyme and electron acceptor. The total content of the hydrophilic polymer in the first and the second layer amounted to 231% by weight of the glucose oxidase.

Sample solutions for the glucose sensor were glucose solutions containing glucose at a concentration of 0 to 800 mg/dl, formulated with pure water, 100 mM phosphate buffer solution at pH5, or 100 mM phosphate buffer solution at pH7. As in Example 1, one min after supply of the sample solution (3 $\mu$l) from the sample supply port 13, a voltage of +0.5 V was applied between the working electrode 4 and the counter electrode 5 of the electrode system. Measurement of a current value after 5 sec showed that the obtained values were dependent on the glucose concentrations in the glucose solutions formulated with pure water, 100 mM phosphate buffer solution at pH5, or 100 mM phosphate buffer solution at pH7. The current value responsive to the glucose concentration was substantially equal between the pure water glucose solution, PBS glucose solution pH5 and PBS glucose solution pH7.

Blood was used as another sample solution for the glucose sensor. One min after sample supply, a voltage of +0.5 V was applied between the working electrode 4 and the counter electrode 5 of the electrode system. Similarly, measurement of the current value after 5 sec showed current values dependent on the glucose concentration in the blood sample solution. The current value responsive to the glucose concentration in the blood sample solution was about 97% of the current value responsive to the glucose solution of the same glucose concentration.

Although the glucose sensor was used in the foregoing examples, the present invention is applicable to various biosensors utilizing an enzyme-related reaction system, such as alcohol sensor, sucrose sensor, cholesterol sensor, lactate sensor, fructose sensor, and the like.

The enzyme is not limited to the glucose oxidase, and other enzymes, such as glucose dehydrogenase, alcohol oxidase, alcohol dehydrogenase, cholesterol oxidase, cholesterol dehydrogenase, lactate oxidase, lactate dehydrogenase, fructose dehydrogenase, ascorbic acid oxidase, and bilirubin oxidase, may also be used.

In the foregoing examples, the preventive effect of the first layer containing the hydrophilic polymer against the adsorbance of protein onto the surface of the electrode system was described using CMC as the hydrophilic polymer, similar preventive effect may be obtained by any cellulose ethers, such as hydroxyethyl cellulose, carboxyethyl cellulose, hydroxypropyl cellulose, carboxyethylmethyl cellulose, and the like.

Furthermore, although the foregoing examples used CMC, hydroxyethyl cellulose, and carboxyethyl cellulose as the hydrophilic polymer contained in the second layer, a similar preventive effect may be obtained by any cellulose ethers, such as hydroxypropyl cellulose, carboxyethylmethyl cellulose, and the like, as well as amylose, starch and its derivatives.

On the other hand, other than the potassium ferricyanide used in the foregoing examples, p-benzoquinone, phenazine methosulfate, indophenol and its derivatives, potassium β-naphthoquinone-4-sulfonate, methylene blue, ferrocene and its derivatives may be used as the electron acceptor.

Although the foregoing examples used water as the solvent for dissolving the hydrophilic polymer, enzyme and electron acceptor, various buffer solutions, such as phosphate buffer solution, citrate buffer solution, acetate buffer solution, tris (hydroxymethyl) aminomethane hydrochloride buffer solution, and the like may also be used.

In the above-mentioned examples, the enzyme and the electron acceptor were dissolved in the sample solution, but these components may be fixed to make them insoluble in the sample solution.

Formation of an additional layer containing lecithin over the reaction layer may be helpful for smooth introduction of the sample.

In the foregoing examples, although a bipolar electrode system comprised of a working electrode and a counter electrode was used, a triple electrode system comprised of a reference electrode in addition to the above-mentioned two electrodes may facilitate more precise measurement.

As discussed above, the present invention can provide a biosensor that facilitates quantitation of a target substance with good accuracy, free from the effect of any components existing in the sample solution other than the substrate.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

We claim:

1. A biosensor comprising:

an electrically insulating base plate, an electrode system including a working electrode and a counter electrode provided on said base plate, and a reaction layer containing a hydrophilic polymer, 0.5 to 50 μg of an enzyme and an electron acceptor formed over said electrode system, wherein said reaction layer contains said hydrophilic polymer in a range of 150 to 1,000% by weight of said enzyme, wherein said reaction layer is dissolved in a sample solution comprising an analyte dissolved in an aqueous media prior to detection of a reaction between said enzyme and said analyte, and wherein said reaction layer is essentially soluble in said sample solution.

2. The biosensor in accordance with claim 1, wherein said hydrophilic polymer is selected from the group consisting of carboxymethyl cellulose, carboxyethyl cellulose, hydroxyethyl cellulose, hydroxypropyl cellulose, carboxyethylmethyl cellulose, amylose, and starch.

3. The biosensor in accordance with claim 1, wherein said enzyme is at least one selected from the group consisting of glucose oxidase, glucose dehydrogenase, alcohol oxidase, alcohol dehydrogenase, cholesterol oxidase, cholesterol dehydrogenase, lactate oxidase, lactate dehydrogenase, fructose dehydrogenase, ascorbic acid oxidase, and bilirubin oxidase.

4. The biosensor in accordance with claim 1, wherein said reaction layer is composed of a first layer containing the hydrophilic polymer and a second layer containing the hydrophilic polymer, enzyme and electron acceptor.

5. The biosensor in accordance with claim 1, wherein the hydrophilic polymer included in said reaction layer is at least one selected from the group consisting of carboxymethyl cellulose, carboxyethyl cellulose, hydroxyethyl cellulose, hydroxypropyl cellulose, and carboxyethylmethyl cellulose.

6. The biosensor in accordance with claim 1, wherein an amount of sample solution to be introduced into said biosensor for one measurement is about 3 ul.

* * * * *